US006444629B1

(12) United States Patent
Elliott et al.

(10) Patent No.: US 6,444,629 B1
(45) Date of Patent: Sep. 3, 2002

(54) CLEANSING COMPOSITIONS

(75) Inventors: Russell Philip Elliott, Egham; Nicola Jacqueline Phipps, Green Lane Addlestone, both of (GB); Timothy Woodrow Coffindaffer, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/486,154

(22) PCT Filed: May 26, 1998

(86) PCT No.: PCT/US98/10647

§ 371 (c)(1),
(2), (4) Date: May 11, 2000

(87) PCT Pub. No.: WO99/09947

PCT Pub. Date: Mar. 4, 1999

(30) Foreign Application Priority Data

Aug. 22, 1997 (GB) .............................................. 9717952

(51) Int. Cl.⁷ .............................. C11D 1/37; C11D 1/94
(52) U.S. Cl. ....................... 510/131; 510/119; 510/127; 510/156
(58) Field of Search .................................. 510/131, 199, 510/122, 126, 127, 156

(56) References Cited

U.S. PATENT DOCUMENTS

| | | | |
|---|---|---|---|
| 5,612,025 A | * 3/1997 | Cauwet-Martin et al. | ............ 424/70.17 |
| 5,648,323 A | * 7/1997 | Coffindaffer et al. | ........ 510/122 |
| 5,674,511 A | * 10/1997 | Kacher et al. | .............. 424/401 |
| 5,716,920 A | * 2/1998 | Glenn, Jr. et al. | .......... 510/159 |
| 5,854,293 A | * 12/1998 | Glenn, Jr. | .................... 514/844 |
| 5,869,070 A | * 2/1999 | Dixon et al. | ................. 424/401 |
| 6,028,043 A | * 2/2000 | Glenn, Jr. et al. | .......... 510/159 |

FOREIGN PATENT DOCUMENTS

| | | | |
|---|---|---|---|
| EP | 498716 A1 | * | 10/1996 |
| WO | WO 95/05800 | * | 3/1995 |
| WO | WO 96/17592 | * | 6/1996 |
| WO | WO 96/28140 | * | 9/1996 |
| WO | WO 96/32919 | * | 10/1996 |
| WO | WO 96/37588 | * | 11/1996 |
| WO | WO 97/14406 | * | 4/1997 |

* cited by examiner

*Primary Examiner*—John Hardee
(74) *Attorney, Agent, or Firm*—Marianne Dressman

(57) ABSTRACT

A rinse-off liquid personal cleansing composition comprising surfactant and water wherein the composition comprises less than 8% of a first surfactant selected from a crystallizing anionic surfactant and greater than 3% of a second surfactant selected from non-crystallizing anionic surfactants, amphoteric surfactants, nonionic surfactants, zwitterionic surfactants, and mixtures thereof, and wherein the composition has a Mean Rinse Feel Value of 3.5 or less as measured by the Rinse Feel Panel Test. The personal cleansing compositions of the invention provide excellent rinse feels and skin mildness.

25 Claims, No Drawings

CLEANSING COMPOSITIONS

TECHNICAL FIELD

The present invention relates to cleansing compositions. In particular it relates to mild personal cleansing compositions which display improved rinse feel in combination with good skin feel attributes, and foaming properties which are suitable for simultaneously cleansing and conditioning the skin and/or the hair and which may be used, for example, in the form of foam bath preparations, shower products, skin cleansers, hand, face and body cleansers, shampoos, etc.

BACKGROUND OF THE INVENTION

Mild cosmetic compositions must satisfy a number of criteria including cleansing power, foaming properties and mildness/low irritancy/good feel with respect to the skin, hair and the ocular mucosae. Skin is made up of several layers of cells which coat and protect the underlying tissue. The keratin and collagen fibrous proteins form the skeleton of its structure. The outermost of these layers, referred to as the stratum corneum. Hair similarly has a protective outer coating enclosing the hair fibre which is called the cuticle. Anionic surfactants can penetrate the stratum corneum membrane and the cuticle and, by delipidization destroy membrane integrity and loss of barrier and water retention functions. This interference with skin and hair protective membranes can lead to a rough skin feel and eye irritation and may eventually permit the surfactant to trigger immune response creating irritation.

Ideal cosmetic cleansers should cleanse the skin or hair gently, without disrupting structural lipids and/or drying the hair and skin and without irritating the ocular mucosae or leaving skin taut after frequent use. Most lathering soaps, shower and bath products, shampoos and bars fail in this respect.

Certain synthetic surfactants are known to be mild. However, a major drawback of some mild synthetic surfactant systems when formulated for shampooing or personal cleansing is that they have what can be described as a "slippy" or "non-draggy" rinse feel which is not liked by some consumers. The use of certain surfactants such as potassium laurate, on the other hand, can yield acceptable rinse feel performance but at the expense of clinical skin mildness. These two facts make the selection of suitable surfactants in the rinse feel and mildness benefit formulation process a delicate balancing act.

Thus a need exists for personal cleansing compositions which deliver a "draggy" rinse feel while at the same time having excellent skin mildness, in addition to excellent product characteristics such as lather, cleansing, stability, thickening, rheology and in-use skin feel attributes.

Certain polyalphaolefin oils are known for use in personal cleansing compositions for the skin and hair. References to the use of such oils in personal cleansing formulations are to be found in WO 97/09031, U.S. Pat. No. 5,441,730, WO 94/27574, EP-A-0692244, WO 96/32092 and WO 96/06596. Hydrophobically modified silicones oils are also known for use in personal cleansing compositions and are disclosed for example in JP 05-310540.

Surprisingly, it has now been found that personal cleansing compositions having a "draggy" rinse feel at the same time as having excellent mildness characteristics are provided by a certain combination of so-called "draggy" and "non-draggy" surfactants together with certain water-insoluble oils, such as certain polyalphaolefin oils or hydrophobically modified silicones oils.

Whilst nor wishing to be bound by theory, the "draggy" rinse feel is considered to be associated with an increase in wet skin friction. An important mechanism for action of such oils is considered to be their ability to deposit and change the surface energy of the skin, i.e. making the skin surface more hydrophobic. During rinsing, the water film is considered to be the lubricant for the skin, and as surface hydrophobicity increases so the water film is destabilised and the surface de-wetted. As a result the water film is at first thinned and then displaced, allowing some direct contact between the surfaces. Both changes increase friction and produce "draggy rinsing".

SUMMARY OF THE INVENTION

According to the present invention there is provided a rinse-off personal cleansing composition comprising water and surfactant wherein the composition comprises less than 8% of a first surfactant selected from a crystallizing anionic surfactant and greater than 3% by weight of a second surfactant selected from a non-crystallizing anionic surfactant, amphoteric surfactant, nonionic surfactant and zwitterionic surfactant, and mixtures thereof, and wherein the composition has a Mean Rinse Feel Value of 3.5 or less as measured by the Rinse Feel Panel Test.

The compositions of the present invention provide an improvement in rinse feel while at the same time being exceptionally mild to the skin.

All concentrations and ratios herein are by weight of the cleansing composition, unless otherwise specified. Surfactant chain lengths are also on a weight average chain length basis, unless otherwise specified.

DETAILED DESCRIPTION OF THE INVENTION

The liquid cleansing compositions herein comprise water and surfactants including la crystallizing anionic surfactant and a non-crystallizing anionic surfactant. The compositions herein have a Mean Rinse Feel Value of 3.5 or less as measured by the Rinse Feel Panel Test described hereinbelow. Preferably the composition has a Mean Rinse Feel Value for the composition of 3.25 or less, more preferably of 3.0 or less. In preferred embodiments the composition has a Mean Rinse Feel Value in the range of from 3.5 to 1.0.

As used herein the term "rinse feel" means the feeling of the skin during the process of rinsing lather from the skin after cleansing with a cleansing composition. The type of rinse feel which is provided by the compositions of the present invention can be described by terms such as a "draggy" rinse feel, a "soap like" rinse feel and a "non-slippery" or "non-slimy" rinse feel. Such a "draggy", "soap-like", "non-slippery" or "non-slimy" rinse feel can be detected by an increase in friction between the hand and skin during the process of rinsing lather from the skin.

As used herein the term "water-insoluble" in relation to oils is a material which is substantially insoluble in distilled water at room temperature without the addition of other adjuncts or ingredients such as those detailed herein.

Surfactant

An essential ingredient herein is one or more surfactants. The compositions herein comprise less than 8%, preferably less than 6% by weight of a first surfactant selected from a crystallizing anionic surfactant and greater than 3% by weight of a second surfactant selected from non-crystallizing anionic surfactants, amphoteric surfactants, nonionic surfactants, zwitterionic surfactants, and mixtures thereof.

As used herein the term "crystallizing anionic surfactant" means an anionic surfactant in which the monovalent salt of that surfactant (eg. sodium, potassium or ammonium salt) will precipitate in the presence of calcium ions. Further, the term "crystallizing surfactant" as used herein means a surfactant which will precipitate turning a substantially clear solution turbid if a 10% solution of that surfactant (the 10% solution being at a temperature at which it is substantially clear (between 30 and 50° C., preferably about 30° C.)) is progressively diluted with 3.56 mmol of $Ca^{2+}$ ions (20° d water hardness, at the same temperature as the 10% surfactant solution) at a molar ratio of about 1:1 to about 2:1 surfactant :calcium. This effect may also be observed as a deviation from ideality in the surface tension profile of the surfactant. Crystallizing anionic surfactants provide a "draggy," rinse feel on the skin. The term "non-crystallizing" anionic surfactant .as used herein means an anionic surfactant which does not show the behaviour of a crystallizing surfactant as defined herein above, i.e. one which does not precipitate in the presence of calcium ions. "Non-crystallizing" anionic surfactants generally provide a "slimy" rinse feel on the skin.

Surfactants suitable for inclusion in compositions according to the present invention generally have a lipophilic chain length of from about 6 to about 22 carbon atoms. While not wishing to be bound by theory, the type, length and distribution of the lipophilic chain of the surfactant can impact on the precipitation behaviour of the surfactant. The use of greater than 90% of a single chain length for example and the use of a longer chain length can increase the calcium sensitivity and increase the "draggy" nature of the surfactant. The use of branched and/or short chain lengths and/or broad distributions of chain lengths on the other hand may prevent precipitation and increase the "slimy" nature of the surfactant.

The compositions herein comprise less than 8%, preferably less than 6%, preferably 0% to about 5%, especially 1% to about 5% by weight of a first surfactant which is selected from a "crystallizing" or "draggy" anionic surfactant.

Suitable anionic surfactants of the "crystallizing" or "draggy" type as defined herein include anionic surfactants such as alkyl sulphates, methyl acyl taurates, acyl glycinates, N-acyl glutamates, acylisethionates, alkyl sulfosuccinateos, alkyl phosphate esters, acyl sarcosinates and acyl aspartates, linear alkyl benzene sulfonates, soaps, and alpha-olefin sulfonates, and mixtures thereof.

Preferred "crystallizing" anionic surfactants for use herein include N-acyl glutamates such as lauroyl and myristoyl glutamate, acylisethionates such as lauroyl and myristoyl isethionates and alkyl phosphate esters such as lauryl and myristyl phosphate.

The compositions herein comprise greater than 3%, preferably greater than 5%, preferably from about 5% to about 30%, especially from about 5% to about 20% by weight of a second surfactant selected from a "non-crystallizing" or "non-draggy" surfactant, an amphoteric surfactant, a nonionic surfactant and a zwitterionic surfactant, and mixtures thereof.

Suitable surfactants of "non-crystallizing" or "non-draggy" type as defined herein include ethoxylated alkyl sulphates, alkyl ethoxy carboxylates, alkyl glyceryl ether sulphonates, alkyl ethoxysulphosuccinates, alpha sulphonated fatty acids, their salts and/or their esters, ethoxylated alkyl phosphate ;esters, ethoxylated alkyl glyceryl ether sulfonates, paraffin sulfonates and alkoxy amide sulfonates, and mixtures thereof.

Preferred "non-crystallizing" surfactants for use herein are ethoxylated alkyl sulphates, such as ammonium laureth-3 sulfate.

The total level of anionic surfactant in the compositions herein is preferably from about 5% to about 20%, especially from about 5% to about 15% by weight.

Other suitable surfactants for use in the compositions herein include water-soluble surfactants including nonionic, amphoteric and/or zwitterionic surfactants. Water-soluble in relation to surfactants, as defined herein, means a surfactant having a molecular weight of less than about 20,000 wherein the surfactant is capable of forming a clear isotropic solution when dissolved in water at 0.2% w/w under ambient conditions. Surfactants suitable for inclusion in compositions according to the present invention generally have a lipophilic chain length of from about 6 to about 22 carbon atoms. The total level of surfactant is preferably from about 2% to about 40%, more preferably from about 3% to about 20% by weight, and especially from about 5% to about 15% by weight. The compositions preferably comprise a mixture of anionic with zwitterionic and/or amphoteric. surfactants. The weight ratio of anionic surfactant: zwitterionic and/or amphoteric surfactant is in the range from about 1:10 to about 10:1 preferably from about 1:5 to about 5:1, more preferably from about 1:3 to about 3:1. Other suitable compositions within the scope of the invention comprise mixtures of anionic, zwitterionic and/or amphoteric surfactants with one or more nonionic surfactants.

The compositions according to the present invention may comprise water-soluble nonionic surfactant at levels from about 0.1% to about 20%, more preferably from about 0.1% to about 10%, and especially from about 1% to about 8% by weight. Surfactants of this class include sucrose polyester surfactants, $C_{10}-C_{18}$ alkyl polyglycosides and polyhydroxy fatty acid amide surfactants having the general formula (III).

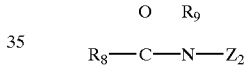

The preferred N-alkyl, N-alkoxy or N-aryloxy, polyhydroxy fatty acid amide surfactants according to formula (III) are those in which $R_8$ is $C_5-C_{31}$ hydrocarbyl, preferably $C_6-C_{19}$ hydrocarbyl, including straight-chain and branched chain alkyl and alkenyl, or mixtures thereof and $R_9$ is typically, hydrogen, $C_1-C_8$ alkyl or hydroxyalkyl, preferably methyl, or a group of formula $—R^1—O—R^2$ wherein $R^1$ is $C_2-C_8$ hydrocarbyl including straight-chain, branched-chain and cyclic (including aryl), and is preferably $C_2-C_4$ alkylene, $R^2$ is $C_1-C_8$ straight-chain, branched-chain and cyclic hydrocarbyl including aryl and oxyhydrocarbyl, and is preferably $C_1-C_4$ alkyl, especially methyl, or phenyl. $Z_2$ is a polyhydroxyhydrocarbyl moiety having a linear hydrocarbyl chain with at least 2 (in the case of glyceraldehyde) or at least 3 hydroxyls (in the case of other reducing sugars) directly connected to the chain, or an alkoxylated derivative (preferably ethoxylated or propoxylated) thereof. $Z_2$ preferably will be derived from a reducing sugar in a reductive ammination reaction, most preferably $Z_2$ is a glycityl moiety. Suitable reducing sugars include glucose, fructose, maltose, lactose, galactose, mannose, and xylose, as well as glyceraldehyde. As raw materials, high dextrose corn syrup, high fructose corn syrup, and high maltose corn syrup can be utilised as well as the individual sugars listed above. These corn syrups may yield a mix of sugar components for $Z_2$. It should be understood that it is by no means intended to exclude other suitable raw materials. $Z_2$ preferably will be selected from the group consisting of $CH_2—(CHOH)_n—CH_2OH$, $CH(CH_2OH)—(CHOH)_{n-1}—CH_2OH$, $CH_2(CHOH)_2(CHOR')CHOH)—CH_2OH$, where n is an integer from 1 to 5, inclusive, and R' is H or a cyclic mono- or poly-saccharide, and alkoxylated derivatives thereof. As noted, most preferred are glycityls wherein n is 4, particularly $-CH_2-(CHOH)_4-CH_2OH$.

The most preferred polyhydroxy fatty acid amide has the formula $R_8(CO)N(CH_3)CH_2(CHOH)_4CH_2OH$ wherein $R_8$ is a $C_6-C_{19}$ straight chain alkyl or alkenyl group. In compounds of the above formula, $R_8$—CO—N< can be, for example, cocoamide, stearamide, oleamide, lauramide, myristamide, capricamide, caprylicamide, palmitamide, tallowamide, etc.

Exemplary non-ionic surfactants suitable for use in the compositions according to the present invention include primary amines such as cocamine (available as Adagen 160D (TM) from Witco) and alkanolamides such as cocamide MEA (available as Empilan CME (TM) from Albright and Wilson), PEG-3 cocamide, cocamide DEA (available as Empilan CDE (TM) from Albright and Wilson), lauramide MEA (available as Empilan LME (TM) from Albright and Wilson), lauramide MIPA, lauramide DEA, and mixtures thereof.

Suitable amphoteric surfactants for use herein include
(a) ammonium derivatives of formula [V]:

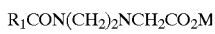

wherein $R_1$ is $C_5-C_{22}$ alkyl or alkenyl, $R_2$ is $CH_2CH_2OH$ or $CH_2CO_2M$, M is H, alkali metal, alkaline earth metal, ammonium or alkanolammonium and $R_3$ is $CH_2CH_2OH$ or H;

(b) aminoalkanoates of formula [VI]

iminodialkanoates of formula [VII]

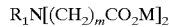

and iminopolyalkanoates of formula (VIII)

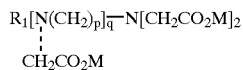

wherein n, m, p, and q are numbers from 1 to 4, and $R_1$ and M are independently selected from the groups specified above; and (c) mixtures thereof.

Suitable amphoteric surfactants of type (a) include compounds of formula (V) in which $R_1$ is $C_{11}H_{23}$. Suitable amphoteric surfactants of type (a) are marketed under the trade name Miranol and Empigen.

In CTFA nomenclature, materials suitable for use in the present invention include cocoamphocarboxypropionate, cocoamphocarboxy propionic acid, cocoamphoacetate, cocoamphodiacetate (otherwise referred to as cocoamphocarboxyglycinate), sodium lauroamphoacetate (otherwise referred to as sodium lauroamphocarboxyglycinate). Specific commercial products include those sold under the trade names of Ampholak 7TX (sodium carboxy methyl tallow polypropyl amine), Empigen CDL60 and CDR 60 (Albright & Wilson), Miranol H2M Conc. Miranol C2M Conc. N.P., Miranol C2M Conc. O.P., Miranol C2M SF, Miranol CM Special, Miranol Ultra L32 and C32 (Rhône-Poulenc); Alkateric 2CIB (Alkaril Chemicals); Amphoterge W-2 (Lonza, Inc.); Monateric CDX-38, Monateric CSH-32 (Mona Industries); Rewoteric AM-2C (Rewo Chemical Group); and Schercotic MS-2 (Scher Chemicals).

It will be understood that a number of commercially-available amphoteric surfactants; of this type are manufactured and sold in the form of electroneutral complexes with, for example, hydroxide counterions or with anionic sulfate or sulfonate surfactants, especially those of the sulfated $C_8-C_{18}$ alcohol, $C_8-C_{18}$ ethoxylated alcohol or $C_8-C_{18}$ acyl glyceride types. Preferred from the viewpoint of mildness and product stability, however, are compositions which are essentially free of (non-ethoxylated) sulfated alcohol surfactants. Note also that the concentrations and weight ratios of the amphoteric surfactants are based herein on the uncomplexed forms of the surfactants, any anionic surfactant counterions being considered as part of the overall anionic surfactant component content.

Examples of suitable amphoteric surfactants of type (b) include N-alkyl polytrimethylene poly-, carboxymethylamines sold under the trade names Ampholak X07 and Ampholak 7CX by Berol Nobel and also salts, especially the triethanolammonium salts and salts of N-lauryl-beta-amino propionic acid and N-lauryl-imino-dipropionic acid. Such materials are sold under the trade name Deriphat by Henkel and Miratraine by Rhône-Poulenc.

The compositions herein can also contain from about 0.1% to about 20%, more preferably from about 0.1% to about 10%, and especially from about 1% to about 8% by weight of a zwitterionic surfactant.

Water-soluble betaine surfactants suitable for inclusion in the compositions of the present invention include alkyl betaines of the formula $R_5R_6R_7N^+ (CH_2)_nCO_2M$ and amido betaines of the formula (IX)

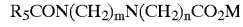

wherein $R_5$ is $C_5-C_{22}$ alkyl or alkenyl, $R_6$ and $R_7$ are independently $C_1-C_3$ alkyl, M is H, alkali metal, alkaline earth metal, ammonium or alkanolammonium, and n, m are each numbers from 1 to 4. Preferred betaines include cocoamidopropyldimethylcarboxymethyl betaine, commercially available from TH Goldschmidt under the tradename Tego betaine, and laurylamidopropyldimethylcarboxymethyl betaine, commercially available from Albright and Wilson under the tradename Empigen BR and from TH Goldschmidt under the tradename Tegobetaine L10S.

Water-soluble sultaine surfactants suitable for inclusion in the compositions of the present invention include alkylamido sultaines of the formula;

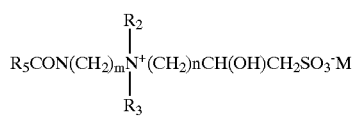

wherein $R_1$ is $C_7$ to $C_{22}$ alkyl or alkenyl, $R_2$ and $R_3$ are independently $C_1$ to $C_3$ alkyl, M is H, alkali metal, alkaline earth metal, ammonium or alkanolammonium and m and n are numbers from 1 to 4. Suitable for use herein is coco amido propylhydroxy sultaine which is commercially available under the tradename Miratraine CBS from Rhone-Poulenc.

Water-soluble amine oxide surfactants suitable for inclusion in the compositions of the present invention include alkyl amine oxide $R_5R_6R_7NO$ and amido amine oxides of the formula

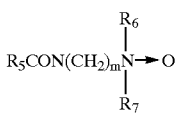

wherein $R_5$ is $C_{11}$ to $C_{22}$ alkyl or alkenyl, $R_6$ and $R_7$ are independently $C_1$ to $C_3$ alkyl, M is H, alkali metal, alkaline earth metal, ammonium or alkanolammonium and m is a number from 1 to 4. Preferred amine oxides include cocoamidopropylamine oxide, lauryl dimethyl amine oxide and myristyl dimethyl amine oxide.

Optional Ingredients

The compositions herein can additionally comprise a wide variety of optional ingredients. Non-limiting examples of such ingredients are described below.

A preferred material, in particular for providing compositions having a "draggy" rinse feel is a water-insoluble oil. Suitable water-insoluble oils for use in the personal cleansing compositions of the present invention include (a) highly branched polyalphaolefins having the following formula:

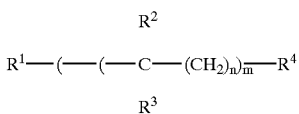

wherein $R_1$ is H or $C_1$–$C_{20}$ alkyl, $R^4$ is $C_1$–$C_{20}$ alkyl, $R^2$ is H or $C_1$–$C_{20}$, and $R^3$ is frog $C_5$–$C_{20}$, n is an integer from 0 to 3 and m is an integer of from 1 to 1000 and having a number average molecular weight of from about 1000 to about 25,000, preferably from about 2000 to about 6000, more preferably from about 2500 to about 4000. Preferably the polyalphaolefins of type (a) use herein have a viscosity of from about 300 cst to about 50,000 cst, preferably from about 1000 cst to about 12,000 cst, more preferably from about 1000 cst to about 4000 cst at 40° C. using the ASTM D-445 method for measuring viscosity. The oils of type (a) may also have a degree of unsaturation, but are preferably saturated.

Examples of such oils include polydecene oils such as those commercially available from Mobil Chemical Company, P.O. Box 3140, Edison, N.J. 08818, USA, under the tradename Puresyn 100.

Other suitable water-insoluble oils for use herein include those of type (b) which are polyalphaolefins having the following formula:

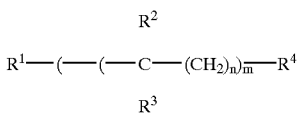

wherein $R^1$ is H or $C_1$–$C_4$ alkyl, $R^4$ is $C_1$–$C_4$ alkyl, $R^2$ is H or $C_1$–$C_4$ alkyl or $C_2$–$C_4$ alkenyl, and $R^3$ is H or $C_1$–$C_4$ alkyl or $C_2$–$C_4$ alkenyl, n is an integer from 0 to 3 and m is an integer of from 1 to 1000 and having a number average molecular weight of from about 600 to about 1000, preferably from about 750 to about 1000, especially from about 800 to about 1000. Preferably the branched alk(en)yl materials of type (b) have a viscosity in the range of from about 500 cst to about 50,000 cst, preferably from about 1000 cst to about 10,000 cst measured at 40° C. using the ASTM method D-445 for measuring viscosity. The oils of type (b) may be unsaturated or saturated.

Suitable alk(en)yl materials of type (b) for use herein are polymers of butene, isoprene, terpene, styrene or isobutene, preferably butene or isobutene.

Examples of alk(en)yl oils of type (b) include polybutene oils such as those commercially available from Amoco under the tradename Indopol 40 and Indopol 100, and polyisobutene oils such as Permethyl 104A from Presperse Inc. and Parapol 950 from Exxon Chemical Inc.

Also suitable for use herein are hydrophobically modified silicones having the following formula:

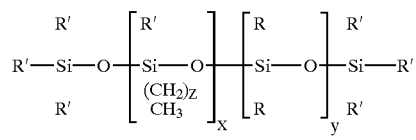

wherein R is $C_1$–$C_4$ alkyl or phenyl, R' is C1–C20 alkyl or phenyl, z is 5 to 21, and x has a number average value in the range of from about 20 to 400, y has a number average value in the range of from about 0 to about 10 and x+y lies in the range of 30 to 400. Preferred materials have values for x of from 40 to 200, preferably 60 to 100, values for y of from 0 to 5, preferably 0, and values for the sum of x and y of from 60 to 100. The alkylene chain z may be linear or branched. In addition, the silicone backbone of the hydrophobically modified silicone may contain a small degree of branching to yield a resin (eg. MDQ or MDT resins).

Examples of such oils include those hydrophobically modified silicones available from GE Silicones under the tradename SF1632 (C16–C18 alkyl methicone), and octyl and decyl methicone.

Mixtures of the above water-insoluble oils are also suitable for use herein.

Particularly preferred from the viewpoint of improving rinse feel of the composition is a highly branched polyalphaolefin material of type (a) having a number average molecular weight of from about 2500 to about 4000 and a/viscosity of from about 100 cst to about 2000 cst (ASTM D-445 at 45° C.) such as that commercially available from Mobil under the tradename Puresyn 100.

In preferred embodiments the number average particle size for the water-insoluble oil used herein lies in the range of from about 1 to about 500 microns, preferably from about 5 to 200 microns, more preferably from about 5 to 50 microns and especially from about 5 to 20 microns.

It is preferable for the compositions herein to provide not only a "draggy" rinse feel gut also a "non-tacky" or "non-sticky" feeling on the skin on rinsing. Therefore it is preferable to use water-insoluble oils which can be described a "non-tacky". The degree of tackiness for water-insoluble oils can be measured by the Tackiness Technical Test Method detailed below.

In preferred embodiments the water-insoluble oil used herein has a Tackiness Index of 120% to Viscasil 5M (Dimethicone) or less as measured by the Tackiness Technical Test Method described herein below. More preferred are those with a Tackiness Index of 110% to Viscasil 5M (Dimethicone) or less. Especially preferred are those with a Tackiness Index of 100% to Viscasil 5M (Dimethicone) or less, especially from 1% to 100%.

Tackiness Technical Test Method

The Tackiness Technical Test Method described herein was developed using basic tack theory. The basic theory of tack is summarised in the Stefan equation which describes the viscous resistance of separation for two discs connected by a thin "squeeze film" of liquid. This is also used in other technology areas where tack assessment is critical, e.g. printing inks. Reference to basic tack theory can be found in the journal article by Phillips, J. C. and Chaing, A. C., "Low Speed Tack Measurements of Fluids and Inks", J. Applied Polymer Science, 1995, 58, 881–895.

A simplified form of the Stefan equation is shown below for the maximum force, F, applied for time, t, to separate discs having a radius r connected by a liquid film having a thickness h and viscosity $\eta$:

$$F = \frac{3 \cdot \pi \cdot \eta r^4}{8 \cdot t \cdot h^2} \quad (1)$$

From this equation, and when the surfaces are separated at a speed v, the separation force becomes:

$$F = k.\eta.v \quad (2)$$

where k is a constant if h and r are fixed in a series of comparative experiments.

This is the basis for determining the relative tackiness of the oils.

The instrument used is an Instron 4301 Tensile Tester, fitted with 10N load cell and 10 mm diameter smooth steel plate on the moving crosshead. The fixed lower plate is also smooth steel and has a compliant rubber spring (56N/mm) and levelling device attaching it to the instrument base. The same plates and spring assembly are used for a set of comparison measurements. The plates are brought close together and set parallel using the levelling device. The contact force is calculated for each oil to give a consistent film thickness from the equation:

$$F = 0.0726.\eta \quad (3),$$

where $\eta$ is the oil viscosity in Pa.s, F is the contact force in N. The machine is set to stop at a compressive force of F. Approximately three drops of oil are placed on the bottom plate, directly below the top plate. The plates are brought together, maintaining the required force for one minute. The tensile speed is set to 1 mm/min and the maximum force is recorded as the tackiness observation. The plates are brought together again and a total of three observations are collected. As a check for outlier observations, the range/mean for the three observations should be less than 10%. If it is not, a further three observations are collected. Three reference oils are included in each set of comparisons, and these are Indopol H100, Viscasil 5M (Dimethicone) and SF1000. The three oils cover a range of tackiness and are their data are used to determine the relative tackiness of the other oils and to assess method reproducibility. In each experiment the ratio of maximum force for an oil is expressed as a percentage of the value for Viscasil 5M (Dimethicone), and this is the Tackiness Index. When correctly set up a coefficient of variation of less than 15% is expected in these data. The significant differences from a set of oils are determined using one way ANOVA of log transformed force data.

Results

1. Squeeze force conditions for Tack Measurement

| Oil Sample | Viscosity Pa (25° C.) | Squeeze Force (N for 1 min) |
| --- | --- | --- |
| Puresyn 100[1] | 2.90 | 0.23 |
| Puresyn 40[1] | 0.77 | 0.06 |
| Indopol H100[2] | 21.0 | 1.52 |
| Indopol H40[2] | 8.4 | 0.61 |
| SF1000 (Dimethicone)[3] | 1.1 | 0.08 |
| Viscasil 5M (Dimethicone)[3] | 5.34 | 0.39 |
| Permethyl 104A[4] | 21.0 | 1.52 |
| Decyl Methicone[3] | 0.98 | 0.07 |
| Octyl Methicone[3] | 0.632 | 0.05 |

2. Mean Separation Force at a separation speed of 1 mm/min

| Oil Sample | Mean Separation Force N) | Tackiness Index to Viscasil 5M[3] (Dimethicone) |
| --- | --- | --- |
| Puresyn 100[1] | 2.44 | 84.4 |
| Puresyn 40[1] | 1.11 | 38.4 |
| Indopol H100[2] | 5.93 | 205.2 |
| Indopol H40[2] | 4.04 | 139.8 |
| SF1000 (Dimethicone)[3] | 1.34 | 46.4 |
| Viscasil 5M (Dimethicone)[3] | 2.89 | 100.0 |
| Permethyl 104A[4] | 6.48 | 224.2 |
| Decyl Methicone[3] | 1.18 | 40.8 |
| Octyl Methicone[3] | 0.90 | 31.1 |

In the statistical analysis each oil is significantly (95%) different for tackiness.

3. Tackiness Index reproducibility from five separate experiments

| Oil Sample | Mean Tackiness Index to Viscasil 5M[3] (Dimethicone) | Cooefficient of Variation | 95% Confidence Limits | |
| --- | --- | --- | --- | --- |
| | | | Lower Limit | Upper Limit |
| Indopol H100[2] | 217.2 | 13.1 | 204.5 | 229.9 |
| SF1000 (Dimethicone)[3] | 49.8 | 7.1 | 38.5 | 61.1 |

1. Polyalphaolegin supplied by Mobil Chemical Co., P.O. Box 3140, Edison, New Jersey 08818, USA
2. Polybutene supplied by Amoco Chemical Co., 200 East Randolph Drive, Chicago, Illinois 60601-7125, USA
3. Supplied by GE Silicones,
4. Polyisobutene supplied by Presperse Inc.

Particularly preferred herein from the viewpoint of providing reduced tackiness rare polyalphaolefin materials of type (a) described above having the following formula:

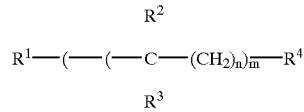

wherein $R^1$ is H or $C_1$–$C_{20}$ alkyl, $R^4$ is $C_1$–$C_{20}$ alkyl, $R^2$ is H or $C_1$–$C_{20}$, and $R^3$ is from $C_5$–$C_{20}$, n is an integer from 0 to 3 and m is an integer of from 1 to 1000 and having a number average molecular weight of from about 2500 to about 4000 and a viscosity of from about 1000 cst to about 2000 cst at 40° C. using the ASTM D-445 method for measuring viscosity, such as that available from Mobil under the tradename Puresyn 100.

The compositions herein preferably comprise from about 0.1% to about 20%, more preferably from about 0.5% to about 10%, especially from about 1% to about 5% by weight of water-insoluble oil.

Another water-insoluble, skin/hair care ingredient suitable for use in the foaming compositions herein is a liquid, polyol carboxylic acid ester.

The polyol ester preferred for use herein is a nonocclusive liquid or liquifiable polyol carboxylic acid ester. These polyol esters are derived from a polyol radical or moiety and one or more carboxylic acid radicals or moieties In other words, these esters contain a moiety derived from a polyol and one or more moieties derived from a carboxylic acid. These carboxylic acid esters can also be derived from a carboxylic acid. These carboxylic acid esters can also be described as liquid polyol fatty acid esters, because the terms carboxylic acid and fatty acid are often used interchangeably by those skilled in the art.

The preferred liquid polyol polyesters employed in this invention comprise certain polyols, especially sugars or sugar alcohols, esterified with at least four fatty acid groups. Accordingly, the polyol starting material must have at least four esterifiable hydroxyl groups. Examples of preferred polyols are sugars, including monosaccharaides and disaccharides, and sugar alcohols. Examples of monosaccharides containing four hydroxyl groups are xylose and arabinose and the sugar alcohol derived from xylose, which has five hydroxyl groups, i.e., xylitol. The monosaccharide, erythrose, is not suitable in the practice of this invention since it only contains three hydroxyl groups, but the sugar alcohol derived from erythrose, i.e., erythritol, contains four hydroxyl groups and accordingly can be used. Suitable five hydroxyl group-containing monosaccharides are galactose, fructose, and sorbose. Sugar alcohols containing six —OH groups derived from the hydrolysis products of sucrose, as well as glucose and sorbose, e.g., sorbitol , are also suitable. Examples of disaccharide polyols which can be used include maltose, lactose, and sucrose, all of which contain eight hydroxyl groups.

Preferred polyols for preparing the polyesters for use in the present invention are selected from the group consisting of erythritol, xylitol, sorbitol, glucose, and sucrose. Sucrose is especially preferred.

The polyol starting material having at least four hydroxyl groups is esterified on at least four of the —OH groups with a fatty acid containing from about 8 to about 22 carbon atoms. Examples of such fatty acids include caprylic, capric, lauric, myristic, myristoleic, palmitic, palmitoleic, stearic, oleic, ricinoleic, linoleic, linolenic, eleostearic, arachidic, arachidonic, behenic, and erucic acid. The fatty acids can be derived from naturally occurring or synthetic fatty acids; they can be saturated or unsaturated, including positional and geometrical isomers. However, in order to provide liquid polyesters preferred for use herein, at least about 50% by weight of the fatty acid incorporated into the polyester molecule should be unsaturated. Oleic and linoleic acids, and mixtures thereof, are especially preferred.

The polyol fatty acid polyesters useful in this invention should contain at least four fatty acid ester groups. It is not necessary that all of the hydroxyl groups of the polyol be esterified with fatty acid, but it is preferable that the polyester contain no more than two unesterified hydroxyl groups. Most preferably, substantially all of the hydroxyl groups of the polyol are esterified with fatty acid, i.e., the polyol moiety is substantially completely esterified. The fatty acids esterified to the polyol molecule can be the same or mixed, but as noted above, a substantial amount of the unsaturated acid ester groups must be present to provide liquidity To illustrate the above points, a sucrose fatty triester would not be suitable for use herein because it does not contain the required four fatty acid ester groups. A sucrose tetra-fatty acid ester would be suitable, but is not preferred because it has more than two unesterified hydroxyl groups. A sucrose hexa-fatty acid ester would be preferred because it has no more than two unesterified hydroxyl groups. Highly preferred compounds in which all the hydroxyl groups are esterified with fatty acids include the liquid sucrose octa-substituted fatty acid esters.

The following are non-limiting examples of specific polyol fatty acid polyesters containing at least four fatty acid ester groups suitable for use in the present invention: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose hepatoleate, sucrose octaoleate, and mixtures thereof.

As noted above, highly preferred polyol fatty acid esters are those wherein the fatty acids contain from about 14 to about 18 carbon atoms.

The preferred liquid polyol polyesters preferred for use herein have complete melting points below about 30° C., preferably below about 27.5° C., m ore preferably below about 25° C. Complete melting points reported herein are measured by Differential Scanning Calorimetry (DSC).

The polyol fatty acid polyesters suitable for use herein can be prepared by a variety of methods well known to those skilled in the art. These methods include: transesterification of the polyol with methyl, ethyl or glycerol fatty acid esters using a variety of catalysts; acylation of the polyol with a fatty acid chloride; acylation of the polyol with a fatty acid anhydride; and acylation of the polyol with a fatty acid, per se. See U.S. Pat. No. 2,831,854; U.S. Pat. No. 4,005,196, to Jandacek, issued Jan. 25, 1977; U.S. Pat. No. 4,005,196, to Jandacek, issued Jan. 25, 1977.

Polymeric Cationic Conditioning Agent

The compositions according to the present invention can optionally include a polymeric cationic conditioning agent. Polymeric cationic conditioning agents are valuable in the compositions according to the present invention for provision of desirable skin feel attributes. The polymeric skin conditioning agent is preferably present at a level from about 0.01% to about 5%, preferably from about 0.01% to about 3% and especially from about 0.01% to about 2% by weight.

Suitable polymers are high molecular weight materials (mass-average molecular weight determined, for instance, by light scattering, being generally from about 2,000 to about 5,000,000, preferably from about 5,000 to about 3,000,000 more preferably from 100,000 to about 1,000, 000).

Representative classes of polymers include cationic guar gums, cationic polysaccharides; cationic homopolymers and copolymers derived from acrylic and/or methacrylic acid; cationic cellulose resins, quaternized hydroxy ethyl cellulose ethers; cationic copolymers of dimethyldiallylammonium chloride and acrylamide and/or acrylic acid; cationic homopolymers of dimethyldiallylammonium chloride; copolymers of dimethyl aminoethylmethacrylate and acrylamide, copolymers of dimethyldiallylammonium chloride and acrylamide, acrylic acid/dimethyldiallylammonium chloride/acrylamide copolymers, quaternised vinyl pyrrolidone acrylate or methacrylate copolymers of amino alcohol, quaternized copolymers of vinyl pyrrolidone and dimethylaminoethylmethacrylamide, vinyl pyrollidone/vinyl imidazolium methochloride copolymers and polyalkylene and ethoxypolyalkylene imines; quaternized silicones, terpolymers of acrylic acid, methacrylamidopropyl trimethyl ammonium chloride and methyl acrylate, and mixtures thereof.

By way exemplification, cationic polymers suitable for use herein include catonic guar gums such as hydroxypropyl trimethyl ammonium guar gum (d.s. of from 0.11 to 0.22) available commercially under the trade names, Jaguar C-14-S(RTM) and Jaguar C-17(RTM) and also Jaguar C-16 (RTM), which contains hydroxypropyl substituents (d.s. of from 0.8–1.1) in addition to the above-specified cationic groups, and quaternized hydroxy ethyl cellulose ethers available commercially under the trade names Ucare Polymer JR-30M, JR-400, LR400, Catanal (RTM) and Celquat. Other suitable cationic polymers are homopolymers of dimethyldiallylammonium chloride available commercially under the trade name Merquat 100, copolymers of dimethyl aminoethylmethacrylate and acrylamide; copolymers of dimethyldiallylammonium chloride and acrylamide, available commercially under the trade names Merquat 550 and Merquat S, acrylic acid/dimethyldiallylammonium chloride/acrylamide copolymers available under the trade name Merquat 3330, and Merquat 3331 terpolymers of acrylic acid, methacrylamidopropyl trimethyl ammonium chloride and methyl acrylate commercially available under the tradename Merquat 2001, quaternized vinyl pyrrolidone acrylate or methacrylate copolymers of amino alcohol available commercially under the trade name Gafquat, for example Polyquaternium 11, 23 and 28 (quaternized copolymers of vinyl pyrrolidone and dimethyl aminoethylmethacrylate—Gafquat 755N and quaternized copolymers of vinyl pyrrolidone and dimethyl aminoethylmethacrylamide—HS-100), vinyl pyrrolidone/vinyl imidazolium methochloride copolymers available under the trade names Luviquat FC370, Polyquaternium 2, and polyalkyleneimines such as polyethylenimine and ethoxylated polyethylenimine.

The compositions of the invention may also contain from about 0.1% to about 20%, preferably from about 1% to about 15%, and more preferably from about 2% to about 10% by weight of an oil derived nonionic surfactant or mixture of oil derived nonionic surfactants. Oil derived nonionic surfactants are valuable in compositions according to the invention for the provision of skin feel benefits both in use and after use. Suitable oil derived nonionic surfactants for use herein include water soluble vegetable and animal-derived emollients such as triglycerides with a polyethyleneglycol chain inserted; ethoxylated mono and di-glycerides, polyethoxyated lanolins and ethoxylated butter derivatives. One preferred class of oil-derived nonionic surfactants for use herein have the general formula (XII)

$$RCOCH_2CH(OH)CH_2(OCH_2CH_2)_nOH$$

wherein n is from about 5 to about 200, preferably from about 20 to about 100, more preferably from about 30 to about 85, and wherein R comprises an aliphatic radical having on average from about 5 to 20 carbon atoms, preferably from about 7 to 18 carbon atoms.

Suitable ethoxylated oils and fats of this class include polyethyleneglycol derivatives of glyceryl cocoate, glyceryl caproate, glyceryl caprylate, glyceryl tallowate, glyceryl palmate, glyceryl stearate, glyceryl laurate, glyceryl oleate, glyceryl ricinoleate, and glyceryl fatty esters derived from triglycerides, such as palm oil, almond oil, and corn oil, preferably glyceryl tallowate and glyceryl cocoate.

Suitable oil derived nonionic surfactants of this class are available from Croda Inc. (New York, USA) under their Crovol line of materials such as Crovol EP40 (PEG 20 evening primrose glyceride), Crovol EP 70 (PEG 60 evening primrose glyceride) Crovol A-40 (PEG 20 almond glyceride), Crovol A-70 (PEG 60 almond glyceride), Crovol M-40 (PEG 20 maize glyceride) Crovol M-70 (PEG 60 maize glyceride), Crovol PK-40 (PEG 12 palm kernel glyceride), and Crovol PK-70 (PEG 45 palm kernel glyceride) and under their Solan range of materials such as Solan E, E50 and X polyethoxylated lanolins and Aqualose L-20 (PEG 24 lanolin alcohol) and Aqualose W15 (PEG 15 lanolin alcohol) available from Westbrook Lanolin. Further suitable surfactants of this class are commercially available from Sherex Chemical Co. (Dublin, Ohio, USA) under their Varonic LI line of surfactants and from Rewo under their Rewoderm line of surfactants. These include, for example, Varonic LI 48 (polyethylene glycol (n=80) glyceryl tallowate, alternatively referred to as PEG 80 glyceryl tallowate), Varonic LI 2 (PEG 28 glyceryl tallowate), Varonic LI 420 (PEG 200 glyceryl tallowate), and Varonic LI 63 and 67 (PEG 30 and PEG 80 glyceryl cocoates), Rewoderm LI5-20 (PEG-200 palmitate), Rewoderm LIS-80 (PEG-200 palmitate with PEG-7 glyceryl cocoate) and Rewoderm LIS-75 (PEG-200 palmitate with PEG-7 glyceryl cocoate) and mixtures thereof. Other oil-derived emollients suitable for use are PEG derivatives of corn, avocado, and babassu oil, as well as Softigen 767 (PEG(6) caprylic/capric glycerides).

Also suitable for use herein are nonionic surfactants derived from composite vegetable fats extracted from the fruit of the Shea Tree (Butyrospermum Karkii Kotschy) and derivatives thereof. This vegetable fat, known as Shea Butter is widely used in Central Africa for a variety of means such as soap making and as a barrier cream, it is marketed by Sedermal(78610 Le Perray En Yvelines, France). Particularly suitable are ethoxylated derivatives of Shea butter available from Karlshamn Chemical Co. (Columbos, Ohio, USA) under their Lipex range of chemicals, such as Lipex 102 E-75 and Lipex 102 E-3 (ethoxylated mono, di-glycerides of Shea butter) and from Croda Inc. (New York, USA) under their Crovol line of materials such as Crovol SB-70 (ethoxylated mono, di-glycerides of Shea butter). Similarly, ethoxylated derivatives of Mango, Cocoa and Illipe butter may be used in compositions according to the invention. Although these are classified as ethoxylated nonionic surfactants it is understood that a certain proportion may remain as non-ethoxylated vegetable oil or fat.

Other suitable oil-derived nonionic surfactants include ethoxylated derivatives of almond oil, peanut oil, rice bran oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grapeseed oil, and sunflower seed oil.

Oil derived nonionic surfactants highly preferred for use herein from the viewpoint of optimum mildness and skin feel characteristics are Lipex 102-3 (RTM) (PEG-3 ethoxylated derivatives of Shea Butter) and Softigen 767 (RTM) (PEG-6 caprylic/capric glycerides).

The compositions according to the present invention can also comprise lipophilic emulsifiers as skin care actives.

Suitable lipophilic skin care actives include anionic food grade emulsifiers which comprise a di-acid mixed with a monoglyceride such as succinylated monoglycerides, monostearyl citrate, glyceryl monostearate diacetyl tartrate and mixtures thereof.

The present compositions can also comprise an auxiliary nonionic or anionic polymeric thickening component, especially a water-soluble polymeric materials, having a molecular weight greater than about 20,000. By "water-soluble polymer" is meant that the material will form a substantially clear solution in water at a 1% concentration at 25° C. and the material will increase the viscosity of the water. Examples of water-soluble polymers which may desirably be used as an additional thickening component in the present compositions, are hydroxyethylcellulose, hydroxypropyl cellulose, hydroxypropyl methylcellulose, polyethylene glycol, polyacrylamide, polyacrylic acid, polyvinyl alcohol (examples include PVA 217 from Kurary Chemical Co., Japan), polyvinyl pyrrolidone K-120, dextrans, for example Dextran purified crude Grade 2P, available from D&O Chemicals, carboxymethyl cellulose, plant exudates such as acacia, ghatti, and tragacanth, seaweed extracts such as sodium alginate, propylene glycol alginate and sodium carrageenan. Preferred as the additional thickeners for the present compositions are natural polysaccharide materials. Examples of such materials are guar gum, locust bean gum, and xanthan gum. Also suitable herein preferred is hydroxyethyl cellulose having a molecular weight of about 700,000.

Hydrotrope

The compositions according to the present invention may contain as an optional feature a hydrotrope. Suitable for use herein as hydrotropes are those well, known in the art, including sodium xylene sulphonate, ammonium xylene sulphonate, sodium cumene sulphonate, short chain alkyl sulphate and mixtures thereof. Hydrotrope may be present in the compositions according to the invention at a level of from about 0.01% to about 5%. preferably from about 0.1% to about 4%, more preferably from about 0.5% to about 3% by weight. Hydrotrope, as defined herein, means, a material which, when added to a non-dilute, water-soluble surfactant system can modify its viscosity and rheological profile.

In addition to the water-insoluble oil described above, the compositions of the invention may also include an insoluble perfume or cosmetic oil or wax or a mixture thereof at a level up to about 10%, preferably up to about 3% by weight wherein the oil or wax is insoluble in the sense of being insoluble in the product matrix at a temperature of 25° C.

Suitable insoluble cosmetic oils and waxes for use herein can be selected from water-insoluble silicones inclusive of non-volatile polyalkyl and polyaryl siloxane gums and fluids, volatile cyclic polydimethylsiloxanes, polyalkoxylated silicones, amino and quaternary ammonium modified silicones, rigid cross-linked and reinforced silicones and mixtures thereof, $C_1$–$C_{24}$ esters of $C_8$–$C_{30}$ fatty acids such as isopropyl myristate, myristyl myristate and cetyl ricinoleate, $C_8$–$C_{30}$ esters of benzoic acid, beeswax, saturated and unsaturated fatty alcohols such as behenyl alcohol, hydrocarbons such as mineral oils, petrolatum, squalane and squalene, fatty sorbitan esters (see U.S. Pat. No. 3,988,255, Seiden, issued Oct. 26th 1976), lanolin and oil-like lanolin derivatives, animal and vegetable triglycerides such as almond oil, peanut oil, wheat germ oil, rice bran oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soyabean oil, avocado oil, safflower oil, coconut oil, hazelnut oil, olive oil, grapeseed oil, and sunflower seed oil, and $C_1$–$C_{24}$ esters of dimer and trimer acids such as diisopropyl dimerate, diisostearylmalate, diisostearyldimerate and triisostearyltrimerate.

The viscosity of the final composition (Brookfield DV II, with Cone CP41 or CP52, 25° C., neat) is preferably at least about 500 cps, more preferably from about 1,000 to about 50,000 cps, especially from about 1,000 to about 30,000 cps, more especially from about 1,000 to about 15,000 cps.

The cleansing compositions can optionally include other hair or skin moisturizers which are soluble in the cleansing composition matrix. The preferred level of such moisturizers is from about 0.5% to about 20% by weight. In preferred embodiments, the moisturizer is selected from essential amino acid compounds found naturally occurring in the stratum corneum of the skin and water-soluble nonpolyol nonocclusives and mixtures thereof.

Some examples of more preferred nonocclusive moisturizers are squalane, sodium pyrrolidone carboxylic acid, D-panthenol, lactic acid, L-proline, guanidine, pyrrolidone, hydrolyzed protein and other collagen-derived proteins, aloe vera gel, acetamide MEA and lactamide MEA and mixtures thereof.

The compositions herein may also include one or more suspending agents. Suitable suspending agents for use herein include any of several long chain acyl derivative materials or mixtures of such materials. Included are ethylene glycol esters of fatty acids having from about 16 to about 22 carbon atoms. Preferred are the ethylene glycol stearates, both mono and distearate, but particularly the distearate containing less than about 7% of the mono stearate. Other suspending agents found useful are alkanol amides of fatty acids, having from about 16 to 22 carbon atoms, preferably from about 16 to 18 carbon atoms. Preferred alkanol amides are stearic monoethanolamide, stearic diethanolamide, stearic monoisopropanolamide and stearic monoethanolamide stearate.

Still other suitable suspending agents are alkyl ($C_{16}$–$C_{22}$) dimethyl amine oxides such as stearyl dimethyl amino oxide and trihydroxystearin commercially available under the tradename Thixcin (RTM) from Rheox.

The suspending agent is preferably present at a level of from about 0.5% to about 5%, preferably from about 0.5% to about 3%. The suspending agents serves to assist in suspending the water-insoluble oil and may give pearlescence to the product. Mixtures of suspending agents are also suitable for use in the compositions of this invention.

Compositions according to the present invention may also include an opacifier, or pearlescing agent. Such materials may be included at a level of from about 0.01% to about 5%, preferably from about 0.2% to about 1.3% by weight.

Opacifiers/pearlescers suitable for inclusion in the compositions of the present invention include: titanium dioxide, $TiO_2$; EUPERLAN 810 (RTM); TEGO-PEARL (RTM); long chain ($C_{16}$–$C_{22}$) acyl derivatives such as glycol or polyethylene glycol esters of fatty acid having from about 16 to about 22 carbon atoms and up to 7 ethyleneoxy units; alkanolamides of fatty acids, having from about 16 to about 22 carbon atoms, preferably about 16 to 18 carbon atoms such as stearic monoethanolamide, stearic diethanolamide, stearic monoisopropanolamide and stearic monoethanolamide and alkyl ($C_{16}$–$C_{22}$) dimethyl amine oxides such as stearyl dimethyl amine oxide.

In preferred compositions the opacifier/pearlescer is present in the form of crystals. In highly preferred compositions the opacifier/pearlescer is a particulate polystyrene dispersion having a particle size of from about 0.05 microns to about 0.45 microns, preferably from about 0.17 microns to about 0.3 microns, such dispersions being preferred from the viewpoint of providing optimum rheology and shear-thinning behaviour. Highly preferred, is styrene acrylate copolymer and OPACFIER 680 (RTM) commercially available from Morton International.

A number of additional optional materials can be added to the cleansing compositions each at a level of from about 0.1% to about 2% by weight. Such materials include proteins and polypeptides and derivatives thereof; water-soluble or solubilizable preservatives such as DMDM Hydantoin, Germall 115, methyl, ethyl, propyl and butyl esters of hydroxybenzoic acid, EDTA, Euxyl (RTM) K400, natural preservatives such as benzyl alcohol, potassium sorbate and bisabalol; sodium benzoate and 2-phenoxyethanol; other moisturizing agents such as hyaluronic acid, chitin, and starch-grafted sodium polyacrylates such as Sanwet (RTM) IM-1000, IM-1500 and IM-2500 available from Celanese Superabsorbent Materials, Portsmith; Va., USA and described in U.S. Pat. No. 4,076,663; solvents; suitable anti-bacterial agents such as Oxeco (phenoxy isopropanol), Trichlorocarbanilide (TCC) and Triclosan and; low temperature phase modifiers such as ammonium ion sources (e.g. $NH_4Cl$); viscosity control agents such as magnesium sulfate and other electrolytes; colouring agents; $TiO_2$ and $TiO_2$-coated mica; perfumes and perfume solubilizers; and zeolites; such as Valfour BV400 and derivatives thereof and $Ca^{2+}/Mg^{2+}$ sequestrants such as polycarboxylates, amino polycarboxylates, polyphosphonates, amino polyphosphonates, EDTA etc, water softening agents such as sodium citrate and insoluble particulates such as zinc stearate and fumed silica. Water is also present at a level preferably of from about 20% to about 99.89%, preferably from about 40% to about 90%, more preferably at least about 75% by weight of the compositions herein.

The pH of the compositions is preferably from about 3 to about 10, more preferably from about 5 to about 9, especially from about 5 to about 8 and most preferably from about 5 to 7.

The compositions of the present invention can be used for a variety of skin and hair care applications such as shower gels, body washes, hair shampoos, and the like.

The compositions of the present invention may be applied with the hand or preferably with a personal cleansing implement such as a puff. Suitable personal cleansing implements for use with the compositions of the present invention include those disclosed in the following patent documents which are incorporated herein by reference: U.S. Pat. No. 5,144,744 to Campagnoli, issued Sep. 8, 1992, U.S. Pat. No. 3,343,196 to Barnhouse, WO95/26671 to The Procter & Gamble Company, WO95/00116 to The Procter & Gamble Company and WO95/26670 to The Procter & Gamble Company.

The compositions according to the present invention are illustrated by the following non-limiting examples.

| Ingredient | I/% | II/% | III/% | IV/% | V/% |
|---|---|---|---|---|---|
| Narrow Range sodium laureth-3 sulphate (Genopol ZRONR)[1] | — | — | — | — | — |
| Ammonium laureth-3 sulphate (Empicol EAC/TP)[2] | 8.4 | 8.4 | 15 | 15 | 15 |
| Ammonium lauryl sulphate (Empicol AL30)[2] | — | — | — | 5 | 2.0 |
| Lauroamphoacetate (Empigen CDL60P)[2] | 3.6 | 3.6 | 10 | — | 5.0 |
| Na Lauroyl Sarcosinate (Hamposyl L30)[3] | 0.5 | 0.5 | — | — | — |
| Lauramidopropyl betaine Empigen BR)[2] | — | — | — | — | — |
| Cocamido MEA (Empilan CME)[2] | — | — | 1.0 | 1.0 | 1.0 |
| Ethylene Glycol Distearate | 2.0 | 2.0 | 2.0 | 2.0 | 2.0 |
| Trihydroxystearin (Thixcin)[4] | — | — | — | — | — |
| Lauric Acid | — | — | — | — | — |
| Dobanol 235 | 0.4 | 0.4 | — | — | — |
| Water-insoluble oil[6] | 2.0 | 10.0 | 6.0 | 4.0 | 2.0 |
| Perfume | 0.5 | 0.5 | 1.0 | 1.0 | 1.5 |
| EDTA | 0.11 | 0.11 | 0.11 | 0.11 | 0.11 |
| Benzoate | 0.25 | 0.25 | 0.25 | 0.25 | 0.25 |
| DMDM Hydantoin | 0.138 | 0.138 | 0.138 | 0.138 | 0.138 |
| NaCl | 0.5 | 0.5 | 0.5 | 0.5 | 0.5 |
| Citric acid | 0.7 | 0.7 | 1.5 | 0.4 | 1.0 |
| Viscasil D5M (Dimethicone)[7] | — | — | — | — | — |
| Water | to 100 | | | | |

| Ingredient | VI/% | VII/% | VIII/% | IX/% | X/% |
|---|---|---|---|---|---|
| Narrow Range sodium laureth-3 sulphate (Genopol ZRONR)[1] | — | — | 10.0 | — | — |
| Ammonium laureth-3 sulphate (Empicol EAC/TP)[2] | 15 | 8.5 | — | 6.0 | 10.0 |
| Ammonium lauryl sulphate (Empicol AL30)[2] | 5 | 2.0 | — | — | — |
| Lauroamphoacetate (Empigen CDL60P)[2] | 2 | 4.0 | — | 3.0 | — |
| Na Lauroyl Sarcosinate (Hamposyl L30)[3] | — | — | — | 1.5 | — |
| Lauramidopropyl betaine (Empigen BR)[2] | — | — | 5.0 | — | 4.0 |
| Cocamido MEA (Empilan CME)[2] | 1.0 | — | 1.0 | 1.0 | 1.0 |
| Ethylene Glycol Distearate | 2.0 | 2.0 | 2.0 | 2.0 | 2.0 |
| Trihydroxystearin (Thixcin)[4] | — | — | — | — | — |
| Lauric Acid | — | — | — | — | — |
| Dobanol 23[5] | — | — | — | 0.2 | — |
| Water-insoluble oil[6] | 8.0 | 4.0 | 2.0 | 4.0 | 4.0 |
| Perfume | 0.5 | 0.5 | 1.0 | 0.5 | 1.0 |
| EDTA | 0.11 | 0.11 | 0.11 | 0.11 | 0.11 |
| Benzoate | 0.25 | 0.25 | 0.25 | 0.25 | 0.25 |
| DMDM Hydantoin | 0.138 | 0.138 | 0.138 | 0.138 | 0.138 |
| NaCl | 0.5 | 0.5 | 0.5 | 0.5 | 0.5 |
| Citric acid | 0.5 | 0.5 | 0.2 | 0.6 | 0.3 |
| Viscasil D5M (Dimethicone)[7] | — | — | — | — | — |
| Water | to 100 | | | | |

| Ingredient | XI/% | XII/% | XIII/% | XIV/% | XV/% |
|---|---|---|---|---|---|
| Narrow Range sodium laureth-3 sulphate (Genopol ZRONR)[1] | — | — | — | — | — |

-continued

| Ingredient | XI/% | XII/% | XIII/% | XIV/% | XV/% |
|---|---|---|---|---|---|
| Ammonium laureth-3 sulphate (Empicol EAC/TP)[2] | 8.4 | 10.0 | 10.0 | 8.0 | 15 |
| Ammonium lauryl sulphate (Empicol AL30)[2] | — | — | 2.0 | — | 5 |
| Lauroamphoacetate (Empigen CDL60P)[2] | 3.6 | 5.0 | 5.0 | 3.6 | — |
| Na Lauroyl Sarcosinate (Hamposyl L30)[3] | 0.5 | 0.5 | — | 0.5 | — |
| Lauramidopropyl betaine (Empigen BR)[2] | — | — | — | — | — |
| Cocamido MEA (Empilan CME)[2] | — | — | — | — | 1.0 |
| Ethylene Glycol Distearate | — | — | — | 2.0 | 2.0 |
| Trihydroxystearin (Thixcin)[4] | 1.5 | 1.5 | 1.5 | — | — |
| Lauric Acid | 1.5 | — | — | — | — |
| Dobanol 23[5] | — | 1.5 | 1.5 | 0.4 | — |
| Water-insoluble oil[6] | 4.0 | 10.0 | 4.0 | 4.0 | 4.0 |
| Perfume | 1.5 | 0.5 | 1.0 | 0.5 | 1.0 |
| EDTA | 0.11 | 0.11 | 0.11 | 0.11 | 0.11 |
| Benzoate | 0.25 | 0.25 | 0.25 | 0.25 | 0.25 |
| DMDM Hydantoin | 0.138 | 0.138 | 0.138 | 0.138 | 0.138 |
| NaCl | 0.5 | 0.5 | 0.5 | 0.5 | 0.5 |
| Citric acid | 0.7 | 0.7 | 0.7 | 0.7 | 0.4 |
| Viscasil D5M (Dimethicone)[7] | — | — | — | 1.0 | 0.5 |
| Water | to 100 | | | | |

1. Supplied by Hoechst
2. Supplied by Albright & Wilson
3. Supplied by Hampshire Chemicals
4. Supplied by Rheox
5. Supplied by Shell Chemicals
6. The water-insoluble oil in each of the examples can be Indopol 40 and Indopol 100 supplied by Amoco Chemicals, Puresyn 100 supplied by Mobil Chemical Co., Permethyl 104A supplied by Presperse, SF1632, octyl methicone or decyl methicone supplied by GE Silicones
7. Supplied by GE Silicones Method of Manufacture Compositions can be prepared by firstly making a premix of surfactants and a suspending agent. This premix should contain no more than 15%, by weight of total composition, of surfactant. This is done by combining the surfactants (except sarcosinate), a portion of the water, powder preservatives and the pH adjuster with mild agitation. This mixture is then heated up to about 90° C. during which time, fatty alcohol/fatty acid, the suspending agent and sodium chloride are added with agitation.

The mixture is held at high temperatures for five minutes to one hour before being cooled at a controlled rate to approximately 30 to 40° C. via a heat exchanger causing the suspending agent to crystallize out.

To this premix the remaining water is then added followed by the water-insoluble oil, remaining surfactant, liquid preservatives and perfume. This part of the process is done at room temperature using mild agitation to yield the desired droplet size of 5 to 20 microns.

The products provide excellent rinse feel and mildness benefits together with excellent theological attributes in storage, in dispensing and in-use, in combination with good efficacy benefits including skin conditioning, skin moisturising, good product stability, cleansing and lathering.

Rinse Feel Panel Test

In order to measure the effect of the water-insoluble oils on the rinse feel of the compositions of the invention a rinse feel panel test was carried out as described below.

The test involves an expert panel of 8 people who have been specially trained and qualified in carrying out the Rinse Feel Panel Test.

Instruments

The instruments needed for this test are as follows: Timer, 2 ml syringes, Thermometer, Ballot Sheet (2 per panellist), two 20 L plastic containers with taps, a sink with two draining board areas and access to a water hardness system for varying hardness', water having a flow rate of 1600–1800 ml/30 'seconds. (Water temperature and hardness should be controlled and recorded).

Training of Panellists

Each panellist is trained to recognise three different wet skin feels—grades 0, 4 and 8 described below.

Grade 0 (Extremely Draggy)

Ivory (RTM) bar soap is used for grade 0. The water hardness is 16 gpg, and the water temperature is 36±1° C. The inner forearm and both hands are wet for 5 seconds. The soap bar is lathered in one hand for 6 seconds by using fingers to rotate the bar in palm of hand using one full bar rotation pet count. The resulting lather is applied to the inner forearm for 10 rubs in 10 seconds (1 rub=wrist to elbow to wrist) using moderate pressure. The lather is left on the forearm for 30 seconds and the product is rinsed from the hands. The forearm is rinsed under running water for 30 seconds with the flow of water starting at the elbow. After 30 seconds the arm is stroked once from elbow to wrist using light pressure ensuring that this completed below where the water flow starts. The rinse feel experienced represents grade 0.

Grade 4 (Slightly slippery and slightly draggy)

Zest White Water Fresh (RTM) soap syndet bar (commercially available in the US) is used for grade 4. The water hardness is 16 gpg, and the water temperature is 36±1° C. The inner forearm and both hands are wet for 5 seconds. The soap bar is lathered in the hands for 6 seconds using one full bar rotation per count. The resulting lather is applied to the inner forearm for 10 rubs in 10 seconds (1 rub=wrist to elbow to wrist) using moderate pressure. The lather is left on the forearm for 30 seconds and the product is rinsed from the hands. The forearm is rinsed under running water for 10 second with the flow of water starting at the elbow. After 10 seconds the arm is stroked once from elbow to wrist using light pressure ensuring that this completed below where the water flow starts. The rinse feel experienced represents grade 4.

Grade 8 (Extremely Slippery)

Oil of Olay (RTM) Moisturising Body Wash (commercially available in the U.S.) is used for grade 8. The water hardness is 3 gpg, and the water temperature is 36±1° C. The inner forearm and both hands are wet for 5 seconds. 1.7 ml of product is applied into wet hands. The product is lathered in the hands by rubbing palms together in a circular motion for 6 rotations in 6 seconds using one full rotation per count. The resulting lather is applied to the inner forearm for 10 rubs in 10 seconds (1 rub=wrist to elbow to wrist) using moderate pressure. The lather is left on the forearm for 30 seconds and the product is rinsed from the hands. The forearm is rinsed under running water and immediately the arm is stroked once from elbow to wrist using light pressure ensuring that this completed below where the water flow starts. The rinse feel experienced represents grade 8.

Qualification of Panellists

In order to qualify for the rinse feel panel test the panellists must carry out the following qualification test successfully.

The inner forearm and both hands are wet for 5 seconds. 1.7 ml of each product to be graded is applied to wet hands and lathered by rubbing palms together in a circular motion for 6 rotations in 6 seconds (one full rotation per count). The lather is applied to the inner forearm for 10 rubs in 10 seconds (1 rub=wrist to elbow to wrist) using moderate pressure. The lather is left on the forearm for 30 seconds. The product is rinsed from the hands. The forearm is rinsed under running water for 15 seconds with the flow of water starting at the elbow. During this time the wet skin feel will be evaluated at the following time points: 3 seconds, 9 seconds and 15 seconds. This is to be done by stroking the inner forearm from elbow to wrist three times using light pressure and starting below where the water flow starts. Rinsing is stopped after 15 seconds and each wet skin feel evaluation is marked onto the ballot sheet below:

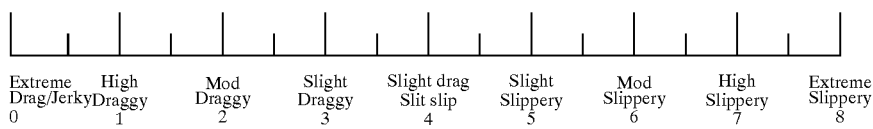

| 0 | 1 | 2 | 3 | 4 | 5 | 6 | 7 | 8 |
|---|---|---|---|---|---|---|---|---|
| Extreme Drag/Jerky | High Draggy | Mod Draggy | Slight Draggy | Slight drag Slit slip | Slight Slippery | Mod Slippery | High Slippery | Extreme Slippery |

Each panellists evaluates blind 2 sets of samples with known qualified panellists results. Each product will be run twice to confirm accuracy. If the panellist does not grade the products correctly twice in a row they have to reassess until they do. However, if after 4 attempts per product they still fail to grade correctly they must be re-trained (section I). When grading is incorrect they cannot be informed of the expected grades, they can only be told if they are too draggy or too slippery.

Each panellist must have at least 3 hours between testing each product set.

All results must be within ±1 grade of the qualified panellists results (see table below). Once the panellists have successfully graded each product twice in a row they are qualified.

Products:

Set 1: LUX Shower Cream for Normal to Dry Skin (Taiwan) versus Taiwan Olay Moisturising Body Wash.

Set 2: Taiwan Olay Moisturising Body Wash versus US Olay Moisturising Body Wash.

Qualification Product Grades for Hard (16 gpg) Water

| PRODUCT | 3 SECONDS GRADE | 9 SECONDS GRADE | 15 SECONDS GRADE |
|---|---|---|---|
| LUX | 4.0 | 3.0 | 2.0 |
| Taiwan Olay Moisturising Body Wash | 6.0 | 5.0 | 4.0 |
| US Olay Moisturising Body Wash | 7.5 | 7.0 | 6.0 |

Qualification Products for Soft (3 gpg) Water:

Set 1: Safaguard Bodywash (China) versus BIORE Natural Moisture (Japan)

Set 2: LUX Shower Cream Normal to Dry Skin (Taiwan) versus US Olay Moisturising Body Wash Qualification Product Grades in 3 gpg water hardness

| PRODUCT | 3 SECOND GRADE | 9 SECOND GRADE | 15 SECOND GRADE |
|---|---|---|---|
| Safaguard Bodywash (China) | 6.5 ± 1.0 | 6.0 ± 1.0 | 5.0 ± 1.0 |
| BIORE Natural Moisture | 6.0 ± 1.0 | 5.0 ± 1.0 | 3.5 ± 1.0 |
| LUX Shower Cream | 6.0 ± 1.0 | 3.5 ± 1.0 | 2.0 ± 1.0 |
| US Olay Moisturising Body Wash | 7.0 ± 1.0 | 6.0 ± 1.0 | 5.5 ± 1.0 |

TEST EVALUATION

Two arm washes can be performed at any one time, one on each arm. Each panellist can evaluate more than one set of test samples per day, but with 3 hour intervals between each set. Moisturisers can not be applied to the forearms before or during the test period.

Always start on the left arm. The inner forearm and both hands are wet for 5 seconds. 1.7 ml of the product to be graded is applied into wet hands. Using moderate pressure the product is lathered in the hands for 6 rotations in 6 seconds (one full rotation per second)? The lather is applied to the inner forearm (from wrist to elbow to wrist) for 10 seconds using moderate pressure. The lather is left on the forearm for 30 seconds. The product is rinsed from the hands. The forearm is rinsed under running water for 15 seconds. with the flow of the water starting at the elbow. During this time the wet skin feel is evaluated at the following time points: 3 seconds, 9 seconds & 15 seconds. This is done by stroking the inner forearm from elbow to wrist three times using light pressure and starting below where the water flows onto the arm. Rinsing is stopped after 15 seconds and each wet skin feel evaluation is marked onto the ballot sheet.

Experimental Design

A randomised incomplete latin square design should be used to compare eight products using eight subjects and two treatment sites per subject.

Calculations

A statistical package capable of performing Analysis of Variance should be used (e.g. Statgraphics Plus version 2.1). The analysis should be performed at 90% significance level, using the evaluation time point as the dependant variable and product, panellist and site as the factors. For 8 subjects this design has 80% power to show differences of 0.71 grades at 90% significance.

Rinse Feel Panel Test Results

Several compositions according to the present invention were tested using the Rinse Feel Panel Test detailed above. In addition, several comparative compositions were also tested. The formulations of each product and Rinse Values are shown below.

Test Products I–IX are compositions according to the present invention.

| Ingredient | I/% | II/% | III/% | IV/% | V/% | VI/% |
|---|---|---|---|---|---|---|
| Ammonium Laureth Sulphate (Empicol EAC/TP[1]) | 8.4 | 8.4 | 8.4 | 8.4 | 8.4 | 8.4 |
| Sodium Lauroamphoacetate (Empigen CDL60P[1]) | 3.6 | 3.6 | 3.6 | 3.6 | 3.6 | 3.6 |
| Sodium Lauroyl Sarcosinate (Hamposyl L30[2]) | 0.5 | 0.5 | 0.5 | 0.5 | 0.5 | 0.5 |
| Ethylene Glycol Distearate[3] | 2 | 2 | 2 | 2 | 2 | 2 |
| Polyalphaolefin (Puresyn 100[4]) | 2 | 4 | 0 | 0 | 0 | 0 |
| Polybutene (Indopol H40[5]) | 0 | 0 | 2 | 0 | 0 | 0 |
| Polybutene (Indopol H100[5]) | 0 | 0 | 0 | 2 | 0 | 0 |
| C16–C18 alkyl methicone (SF1632[6]) | 0 | 0 | 0 | 0 | 2 | 0 |
| Polyisobutene (Permethyl 104A[7]) | 0 | 0 | 0 | 0 | 0 | 2 |
| Tetrasodium EDTA | 0.11 | 0.11 | 0.11 | 0.11 | 0.11 | 0.11 |
| DMDM Hydantoin | 0.138 | 0.138 | 0.138 | 0.138 | 0.138 | 0.138 |
| Sodium Benzoate | 0.25 | 0.25 | 0.25 | 0.25 | 0.25 | 0.25 |
| Citric Acid | 0.7 | 0.7 | 0.7 | 0.7 | 0.7 | 0.7 |
| Perfume | 0.5 | 0.5 | 0.5 | 0.5 | 0.5 | 0.5 |
| Sodium Chloride | 0.5 | 0.5 | 1.4 | 0.5 | 1.4 | 1 |
| Pareth 1213 Alcohol (Dobanol 23[8]) | 0.4 | 0.4 | 0.4 | 0.4 | 0.4 | 0.4 |
| Deionised Water | | | to 100 | | | |
| MEAN RINSE FEEL VALUE | 3.38 | 2.80 | 1.0 | 1.0 | 3.25 | 1.25 |

| Ingredient | VII/% | VIII/% | IX/% |
|---|---|---|---|
| Ammonium Laureth Sulphate (Empicol EAC/TP[1]) | 8.4 | 8.4 | 8.4 |
| Sodium Lauroamphoacetate (Empigen CDL60P[1]) | 3.6 | 3.6 | 3.6 |
| Sodium Lauroyl Sarcosinate (Hamposyl L30[2]) | 0.5 | 0.5 | 0.5 |
| Ethylene Glycol Distearate[3] | 2 | 2 | 2 |
| Decyl Methicone[6] | 0 | 4 | 0 |
| Octyl Methicone[6] | 4 | 0 | 0 |
| Puresyn 100[4] | 0 | 0 | 4 |
| JR30M[9] | 0 | 0 | 0.1 |
| Tetrasodium EDTA | 0.11 | 0.11 | 0.11 |
| DMDM Hydantoin | 0.138 | 0.138 | 0.138 |
| Sodium Benzoate | 0.25 | 0.25 | 0.25 |
| Citric Acid | 0.7 | 0.7 | 0.7 |
| Perfume | 0.5 | 0.5 | 0.5 |
| Sodium Chloride | 0.5 | 0.5 | 0.5 |
| Pareth 1213 Alcohol Dobanol 23[8]) | 0.4 | 0.4 | 0.4 |
| Deionised Water | | to 100 | |
| MEAN RINSE FEEL VALUE | 2.8 | 2.96 | 3.25 |

For comparison the following products were also tested:

| Ingredient | X/% | XI/% | XII/% |
|---|---|---|---|
| Ammonium Laureth Sulphate (Empicol EAC/TP[1]) | 8.4 | 8.4 | 8.4 |
| Sodium Lauroamphoacetate (Empigen CDL60P[1]) | 3.6 | 3.6 | 3.6 |
| Sodium Lauroyl Sarcosinate (Hamposyl L30[2]) | 0.5 | 0.5 | 0.5 |
| Ethylene Glycol Distearate[3] | 2 | 2 | 2 |
| Viscasil 5M[6] (Dimethicone) | 2 | 0 | 0 |
| Puresyn 40[4] | 0 | 4 | 0 |
| Tetrasodium EDTA | 0.11 | 0.11 | 0.11 |
| DMDM Hydantoin | 0.138 | 0.138 | 0.138 |
| Sodium Benzoate | 0.25 | 0.25 | 0.25 |
| Citric Acid | 0.7 | 0.7 | 0.7 |
| Perfume | 0.5 | 0.5 | 0.5 |
| Sodium Chloride | 0.5 | 0.5 | 0.5 |
| Pareth 1213 Alcohol (Dobanol 23[8]) | 0.4 | 0.4 | 0.4 |
| MEAN RINSE FEEL VALUE | 3.94 | 3.63 | 4.2 |

For all of the above results the SEM was from 0.25 to 0.27.
1. Supplied by Albright & Wilson
2. Supplied by Hampshire Chemicals
3. Supplied by Saci
4. Supplied by Mobil Chemical Co.
5. Supplied by Amoco Chemical Co.
6. Supplied by GE Silicones
7. Supplied by Presperse Inc.
8. Supplied by Shell Chemicals
9. Supplied by Amercol

What is claimed is:
1. A rinse-off personal cleansing composition, comprising
(a) less than 8% of a first surfactant selected from crystallizing anionic surfactants;
(b) greater than 3% of a second surfactant selected from non-crystallizing anionic surfactants, amphoteric surfactants, nonionic surfactants, zwitterionic surfactants and mixtures thereof;
(c) from 0.5% to 10% by weight of water-insoluble oil selected from the group consisting of:
(i) polyalphaolefins having the following formula:

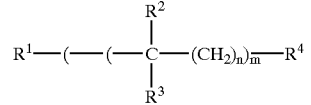

wherein $R^1$ is H or $C_1$–$C_{20}$ alkyl, $R^4$ is $C_1$–$C_{20}$ alkyl, $R^2$ is H or $C_1$–$C_{20}$, and $R^3$ is from $C_5$–$C_{20}$, n is an integer from 0 to 3 and m is an integer of from 1 to 1000 and having a number average molecular weight of from about 2,000 to about 6,000, (ii) polyalphaolefins having the following formula:

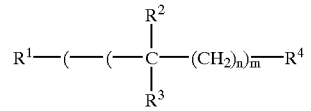

wherein $R^1$ is H or $C_1$–$C_4$ alkyl, $R^4$ is $C_1$–$C_4$ alkyl, $R^2$ is H or $C_1$–$C_4$ alkyl or $C_2$–$C_4$ alkenyl, and $R^3$ is H or $C_1$–$C_4$ alkyl or $C_2$–$C_4$ alkenyl, n is an integer from 0 to 3 and m is an integer of from 1 to 1000 and having a number average molecular weight of from about 600 to about 1000, and (iii) hydrophobically modified silicones having the following formula:

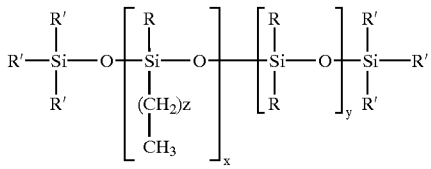

wherein R is $C_1$–$C_4$ alkyl or phenyl, R' is $C_1$–$C_{20}$ alkyl or phenyl, z is 5 to 21, and x has a number average value in the range of from about 20 to 400, y has a number average value in the range of from about 0 to about 10 and x+y lies in the range of 30 to 400;

(d) tip to 10% by weight of petrolatum and mineral oil; and (e) water, wherein the composition has a Mean Rinse Feel Value of 3.5 or less as measured by a Rinse Feel Panel Test.

2. A personal cleansing composition according to claim 1 wherein the composition has a Mean Rinse Feel Value of 3.25 or less.

3. A personal cleansing composition according to claim 2 wherein the composition has a Mean Rinse Feel Value of 3.0 or less.

4. A personal cleansing composition according to claim 1 comprising less than about 5 by weight of crystallizing anionic surfactant.

5. A personal cleansing composition according to claim 1, wherein the composition comprises from about 1% to about 5% by weight of crystallizing anionic surfactants.

6. A personal cleansing composition according to claim 1 wherein the crystallizing anionic surfactant is selected from alkyl sulphates, methyl acyl taurates, fatty acyl glycinates, N-acyl glutamates, acylisethionates, alkyl sulfosuccinates, alkyl phosphate esters, acyl sarcosinates, soaps, alpha-olefin sulfonates, linear alkyl benzene sulfonates and acyl aspartates, and mixtures thereof.

7. A personal cleansing composition according to claim 1 wherein the non-crystallizing anionic surfactant is selected from ethoxylated alkyl suphates, alkyl ethoxy carboxylates, alkyl glyceryl ether sulphonates, alkyl ethoxysulphosuccinates, alpha-sulphonated fatty acids, their salts and/or their esters, ethoxylated alkyl phosphate esters, ethoxylated alkyl glyceryl ether sulfonates, paraffin sulphonates, alkoxy amide sulfonates, and mixtures thereof.

8. A personal cleansing composition according to claim 7 wherein the water-insoluble oil has a tackiness index of 110% to Viscasil 5M (Dimethicone) or less as measured by the Tackiness Technical Test Method.

9. A personal cleansing composition according to claim 1 wherein the water-insoluble oil has a tackiness index of 120% to Viscasil 5M (Dimethicone) or less as measured by the Tackiness Technical Test Method.

10. A personal cleansing composition according to claim 9 wherein the water-insoluble oil has a tackiness index of 100% to Viscasil 5M (Dimethicone) or less as measured by the Tackiness Technical Test Method.

11. A personal cleansing composition according to claim 1 wherein the polyalphaolefin (i) has a number average molecular weight of from about 2,500 to about 4,000.

12. A personal cleansing composition according to claim 1 wherein the polyalphaolefin (i) has a viscosity of from about 1,000 cst to about 12,000 cst at 40° C. (ASTM D-445).

13. A personal cleansing composition according to claim 1 wherein the polyalphaolefin (ii) has a viscosity in the range of from about 500 cst to about 50,000 cst measured at 40° C. using the ASTM method D-445 for measuring viscosity.

14. A personal cleansing composition according to claim 1 wherein the polyalphaolefin (ii) is a polybutene or polyisobutene.

15. A personal cleansing composition to claim 1 wherein the non-crystallizing anionic surfactant comprises ethoxylated alkyl sulfate.

16. A personal cleansing composition according to claim 1 wherein the composition is substantially soap-free.

17. A personal cleansing composition according to claim 1 wherein the water-soluble amphoteric surfactant is selected from ammonium derivatives of the following formula:

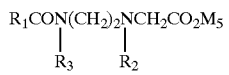

wherein $R_1$ is $C_5$–$C_{22}$ alkyl or alkenyl, $R_2$ is $CH_2CH_2OH$ or $CH_2CH_2M$, M is H, alkali metal, alkaline earth metal, ammonium or alkanolammonium and $R_3$ is $CH_2CH_2OH$ or H.

18. A personal cleansing composition according to claim 1 wherein the zwitterionic surfactant is selected from alkyl betaines of the formula $R_5R_6R_7N^+(CH_2)_nCO_2M$ and amido betaines of the following formula:

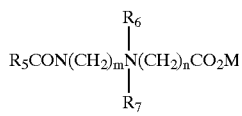

wherein $R_5$ is $C_5$–$C_{22}$ alkyl or alkenyl, $R_6$ and $R_7$ are independently $C_1$–$C_3$ alkyl, M is H, alkali metal, alkaline earth metal, ammonium or alkanolammonium, and n and m are each numbers from 1 to 4.

19. A composition according to claim 1 additionally comprising from about 0.01% to about 5% by weight of cationic polymeric skin conditioning agent selected from the group consisting of cationic guar gums, cationic polysaccharides, cationic homopolymers and copolymers derived from acrylic and/or methacrylic acid, cationic cellulose resins, quaternized hydroxy ethyl cellulose ethers, cationic copolymers of dimethyldiallylammonium chloride and acrylamide and/or acrylic acid, cationic homopolymers of dimethyldiallyiammonium chloride, copolymers of dimethyl aminoethylmethacrylate and acrylamide, acrylic acid/ dimethyldiallylammonium chloride/acrylamide copolymers, quaternized vinyl pyrrolidone acrylate or methacrylate copolymers of amino alcohol, quaternized copolymers of vinyl pyrollidone and dimethylaminoetyl acrylamide, vinyl pyrollidone/vinyl imidazolium methochloride copolymers, polyalkylene imines, ethoxypolyalkylene imines, quaternized silicones, terpolymers of acrylic acid, methacrylamido propyl trimethyl ammonium chloride and methyl acrylate, and mixtures thereof.

20. A personal cleansing composition according to claim 1 wherein the water-insoluble oil has a number average particle diameter of from about 1 micron to about 500 microns.

21. A personal cleansing composition according to claim 1, comprising up to about 3% by weight of the petrolatum and mineral oil.

22. A rinse-off personal cleansing composition, comprising
(a) less than 8% of a first surfactant selected from crystallizing anionic surfactants;
(b) greater than 3% of a second surfactant selected from non-crystallizing anionic surfactants, amphoteric surfactants, nonionic surfactants, zwitterionic surfactants and mixtures thereof;
(c) from 0.5% to 10% by weight of water-insoluble oil selected from the group consisting of polydecene oils, polybutene oils, polyisobutene oils, and C16–C18 alkyl methicones;
(d) up to 10% by weight of petrolatum and mineral oil; and
(e) water,
wherein the composition has a Mean Rinse Feel Value of 3.5 or less as measured by a Rinse Feel Panel Test.

23. A personal cleansing composition according to claim 22 comprising up to about 3% by weight of the petrolatum and mineral oil.

24. A personal cleansing composition according to claim 22 wherein the polydecene oils have a number average molecular weight of from about 2,000 to about 6,000.

25. A personal cleansing composition according to claim 22 comprising less than about 5% by weight of crystallizing anionic surfactant.

* * * * *

UNITED STATES PATENT AND TRADEMARK OFFICE
CERTIFICATE OF CORRECTION

PATENT NO. : 6,444,629 B1
DATED : September 3, 2002
INVENTOR(S) : R.P. Elliot et al.

It is certified that error appears in the above-identified patent and that said Letters Patent is hereby corrected as shown below:

Column 25,
Line 18, "tip" should read -- up --.
Line 30, "5" should read -- 5% --.

Column 26,
Line 58, "dimethylaminoetyl" should read -- dimethylaminoethyl --.

Signed and Sealed this

Twenty-ninth Day of March, 2005

JON W. DUDAS
*Director of the United States Patent and Trademark Office*